(12) United States Patent
Merchez et al.

(10) Patent No.: US 9,140,645 B2
(45) Date of Patent: Sep. 22, 2015

(54) DEVICE AND METHOD FOR MULTIPARAMETRIC MEASUREMENTS OF MICROPARTICLES IN A FLUID

(75) Inventors: Benoit Merchez, Combaillaux (FR); Didier Cremien, Juvignac (FR); Alexandra Urankar, Saint Clement de Riviere (FR)

(73) Assignee: HORIBA ABX SAS, Montpellier cedex 4 (FR)

( * ) Notice: Subject to any disclaimer, the term of this patent is extended or adjusted under 35 U.S.C. 154(b) by 80 days.

(21) Appl. No.: 13/983,082

(22) PCT Filed: Nov. 15, 2011

(86) PCT No.: PCT/FR2011/052643
§ 371 (c)(1),
(2), (4) Date: Aug. 1, 2013

(87) PCT Pub. No.: WO2012/104496
PCT Pub. Date: Aug. 9, 2012

(65) Prior Publication Data
US 2013/0308122 A1 Nov. 21, 2013

(30) Foreign Application Priority Data
Feb. 4, 2011 (FR) ...................................... 11 50930

(51) Int. Cl.
| | |
|---|---|
| *G01J 4/00* | (2006.01) |
| *G01N 21/47* | (2006.01) |
| *G01N 15/14* | (2006.01) |
| *G01N 21/51* | (2006.01) |
| *G01N 21/64* | (2006.01) |
| *G01N 27/04* | (2006.01) |
| *G01N 15/10* | (2006.01) |

(52) U.S. Cl.
CPC .............. *G01N 21/47* (2013.01); *G01N 15/147* (2013.01); *G01N 15/1434* (2013.01); *G01N 21/51* (2013.01); *G01N 21/64* (2013.01); *G01N 21/645* (2013.01); *G01N 27/04* (2013.01); *G01N 2015/1037* (2013.01)

(58) Field of Classification Search
CPC .......... G01N 15/12; G01N 2021/6419; G01N 21/47; G01N 21/6428; G01N 2021/4726
See application file for complete search history.

(56) References Cited

U.S. PATENT DOCUMENTS 3,710,933 A * 1/1973 Fulwyler et al. ............... 209/3.1
4,298,836 A * 11/1981 Groves et al. ................ 324/71.1

(Continued)

FOREIGN PATENT DOCUMENTS

| | | |
|---|---|---|
| EP | 0 564 157 | 10/1993 |
| WO | 2006/053690 | 5/2006 |

(Continued)

*Primary Examiner* — Michael A Lyons
*Assistant Examiner* — Maurice Smith
(74) *Attorney, Agent, or Firm* — Clark & Brody

(57) ABSTRACT

The invention relates to an electro-optical device for measurements of flow for the characterization of microparticles, comprising a measurement chamber (CUM) in which there circulates the flow of the fluid to be characterized, at least two luminous sources (S1,S2) of disjoint spectra, a device for measuring resistivity (RES), and at least three other detectors (D1,D2,D3) each allowing the measurement of an optical parameter, the optical parameters being chosen from among fluorescence (FL), extinction (EXT), wide angle diffraction (SSC) and small angle diffraction (FSC).

14 Claims, 7 Drawing Sheets

(56) References Cited

U.S. PATENT DOCUMENTS

| | | |
|---|---|---|
| 5,138,181 A | 8/1992 | Lefevre et al. |
| 5,934,885 A | 8/1999 | Farrell et al. |
| 7,498,164 B2 * | 3/2009 | Oldham et al. ............ 435/288.7 |
| 2004/0021868 A1 * | 2/2004 | Ortyn et al. .................... 356/419 |
| 2008/0068709 A1 * | 3/2008 | Zimmermann et al. ...... 359/385 |
| 2008/0283754 A1 * | 11/2008 | Nerin et al. .............. 250/339.05 |
| 2009/0059207 A1 * | 3/2009 | Nerin et al. ..................... 356/73 |
| 2010/0238442 A1 * | 9/2010 | Heng et al. .................... 356/343 |

FOREIGN PATENT DOCUMENTS

| | | |
|---|---|---|
| WO | 2007/101932 | 9/2007 |
| WO | 2010/004173 | 1/2010 |

* cited by examiner

DEVICE AND METHOD FOR MULTIPARAMETRIC MEASUREMENTS OF MICROPARTICLES IN A FLUID

BACKGROUND OF THE INVENTION

The present invention relates to the general field of electro-optical flow measuring devices for characterizing microparticles, in particular biological cells, comprising a measurement chamber in which the flow of the fluid to be characterized circulates and the cells to be characterized are contained. This field is based on analysis methods using electrical and optical measurements to count and differentiate cells contained in a sample to be analysed. The present invention more specifically relates to a multiparametric electro-optical device for cell counting and characterization.

The fluid to be characterized is preferably a blood sample, but it may also be a biological fluid of another type such has cerebrospinal fluid, bone marrow etc. The sample may also contain particles of any type which are to be differentiated and counted.

More specifically, the invention concerns devices comprising at least two light sources, a resistivity measurement device, and several detectors allowing the measurement of an optical parameter, typically extinction measurement and side scatter measurement.

These measurements allow the characterization of biological cells contained in the fluid.

With respect to hematopoietic cells, the person skilled in the art knows that morphological analysis of the cell, obtained by volumetry or diffractometry, including extinction and absorption phenomena, allows discrimination between the main cell lines including erythrocytes or red blood cells, thrombocytes or platelets, and leukocytes or white blood cells. This last population is itself sub-divided into several categories e.g. lymphocytes, monocytes, neutrophils, eosinophils and basophils.

To a certain extent, it is possible to assess the level of maturity of these cells by simultaneously determining their volume and apparent absorption in white light such as described in the patent U.S. Pat. No. 5,138,181 filed by the Applicant. An embodiment of a device developed for near-monochromatic light is described for example in the publication WO 2006/053960.

This assessment of cell maturity is important since it allows early diagnosis to be performed. In general, in the absence of any pathology, the majority of the cells present in the circulating blood are mature cells.

For each of the aforementioned cell types, different maturity levels are known. For example, red blood cells, also known as erythrocytes or red blood corpuscles, are first fabricated in the form of proerythroblasts, then basophilic erythroblasts, and then polychromatophilic erythroblasts. The polychromatophilic erythroblasts develop into acidophilic erythroblasts and then into reticulocytes. It is these reticulocytes that finally differentiate into erythrocytes once they have passed into the circulating blood.

White blood cells or leukocytes are derived from bone marrow in a first form of myeloblasts. These myeloblasts then yield pro-granulocytes that will later change into basophilic, eosinophilic, or neutrophilic granulocytes, first unsegmented but then their nuclei increasingly segment as they mature.

These same myeloblasts are also the origin of the monocyte line which will yield monoblasts, promonocytes, and then the monocytes which will pass into peripheral blood.

The pluripotent stem cell, from which the myeloblast originates, also yields the lymphocyte line via differentiation in the form of a lymphoid stem cell of which part of the line, the T-lymphocyte line, will continue its maturation in the thymus and glands and the other part will remain in the bone marrow to give the B-lymphocyte line. These B-lymphocytes, once activated in the form of plasmocytes, produce antibodies to combat pathogenic antigens.

Blood platelets, or thrombocytes, derive from megakaryoblasts, which originate from the myeloid progenitor from which the myeloblast originated, and once they have arrived at their ultimate maturation stage, i.e. thrombocytogenic megakaryocytes, they produce platelets by disintegration of their cytoplasms. The young platelets, reticulated platelets, have an RNA content that is the remainder of their original cell.

The diagnosis of certain pathologies requires ever finer tuned counting and characterization of hematopoietic cells in circulating blood. In particular, it has become important to be able to bring to light specific populations, such as reticulocytes and erythroblasts, which are immature versions of erythrocytes (red blood cells). Similarly, the bringing to light of immature cells, precursors of leukocytes (called immature lymphocytes, monocytes or granulocytes), is becoming increasingly more important. The classification and counting of activated lymphocytes or of reticulated platelets would also make it possible to obtain a veritable improvement in patient diagnosis.

SUBJECT AND SUMMARY OF THE INVENTION

The present invention relates to the development of an analysis device and associated method allowing improved differentiation and hence better counting of each of the particular populations contained in a sample by proposing a flow measuring electro-optical device for the characterization of microparticles comprising a measurement chamber in which there circulates the flow of fluid to be characterized, at least two light sources of disjoint spectra, a device for measuring resistivity and at least three other detectors each allowing measurement of an optical parameter, the optical parameters being chosen from among fluorescence, extinction, wide angle diffraction (side scatter), and small angle diffraction (forward scatter), the electro-optical device being such that:
  the first light source, the least coherent and having the longest wavelength, defines a main optical axis perpendicular to the flow of particles, the main optical axis having two optical assemblies positioned on either side of the chamber, one being an emitting gun that allows the beam emitted by the first source to be shaped, and the other being a receiving gun allowing the signal emitted from the first light source to be collected and being positioned after the measuring chamber;
  the second light source, the most coherent and having the shortest wavelength, defines a secondary optical axis crossing the main optical axis and perpendicular to the flow of particles;
  a first detector placed facing the first source at the extremity of the receiving gun and therefore having light field operation;
  the receiving gun comprises collection optics collecting the beam issued from interaction between the first light source and the particles in the flow towards the first detector, these collection optics being such that over a portion of its pathway, the transmitted light beam is a substantially collimated beam;
  a first dichroic mirror is positioned in the receiving gun at the portion of pathway where the light beam is substantially collimated, so that it partly reflects the light beam issued from the interaction between the second light source and the particles in the flow towards a second detector placed on the pathway of the partly reflected beam;

the emitting gun comprises beam-shaping optics to shape the beam emitted by the first light source, these beam-shaping optics being such that over a portion of its pathway the light beam is substantially a collimated beam; and a second dichroic mirror is placed in the emitting gun between the first light source and the chamber, at the portion of pathway where the light beam is substantially collimated, so as to partly reflect the beam issued from the interaction between the second light source and the particles in the flow, towards a third detector placed on the pathway of the partly reflected beam.

Therefore, as is conventional, the device comprises a micro-orifice through which the particles pass, thereby giving a first measurement of resistivity. Next, thanks to two light sources of which one has a short coherence time, the device allows at least three other measurements to be obtained by means of at least three additional measuring paths.

The device according to the invention comprises an additional measuring path thanks to the insertion, into the emitting gun, of a system of dichroic mirrors allowing additional measurements to be obtained. This innovation renders the device modular and capable of taking multiple measurements within a limited space using a small number of apparatus items. In addition, the measured parameters, if necessary, may be modified whilst maintaining the same structural elements. The obtained particle classification results are distinctly superior to those obtained with known devices. Indeed, with the multiplicity and modularity of accessible parameters, the device according to the invention gives particularly good performance that is sensitive and polyvalent in terms of classification results.

The device according to the invention is very simple to use, low cost, and allows numerous measurements to be obtained, hence numerous cell characteristics.

The device according to the invention, by enabling a broader number of parameter measurements, allows the characterization, differentiation, and absolute counting of the cells contained in a biological sample, including blood samples.

In addition, the light sources being separate, it is easy for them to be combined or not. In particular, this characteristic allows possible compensation problems to be overcome when taking measurements with fluorochromes.

Without drastically modifying the described optical assembly, it is easily possible to obtain additional measurements. For example, small angle diffraction measurements and fluorescence measurements can be obtained, at least as many as there are coherent sources used, which can provide additional information on the nature of the particles being examined.

The device according to the invention is modular in that it allows numerous parameters to be obtained which may be of very different type. For example, it is possible to obtain an extinction measurement, a wide angle diffraction measurement, and a fluorescence measurement. This combination of measurements allows a very good characterization of particles circulating in the measurement chamber to be obtained easily and rapidly.

By adapting the measurements to be taken, the invention allows the very precise measuring of the intracellular haemoglobin content of each erythrocyte population. By extension, the device and the method according to the invention can allow improved analysis of the leukocyte populations in a sample.

According to one particular characteristic, a diffraction/scatter detector is positioned facing the second light source on the other side of the measuring chamber.

This characteristic may be useful in contributing towards cell classification in some particular cases, or more generally to trigger optical measurements.

According to one advantageous characteristic of the invention, the first detector has switchable gain making it able to perform two types of measurement, one in extinction and another chosen from among diffractions and fluorescences.

With this characteristic, it is possible to use a single detector for two parameter measurements involving largely differing light intensities, typically extinction measurement and fluorescence measurement. This characteristic therefore allows a measurement to be added in the emitting gun. The device according to the invention is then even further modular since the first detector can be used either for extinction measurement, or for measurement of another optical parameter. The presence of this twofold measurement within the same spectral band then allows parameters for cell classification to be added without needing to change the measuring equipment, provided there is fluorescence in this spectral band and can be advantageously used for the classification of cells. This avoids having to install clearly distinct paths for fluorescence measurements. According to one particular application, the first detector performs an extinction measurement, the second detector performs a wide angle diffraction measurement and the third detector performs a fluorescence measurement.

The measurements thus obtained allow the counting and differentiation of 8 populations of nucleated cells or of immunophenotyping depending on the analysed samples and the analysis of results conducted after the measurements have been taken.

In another particular application according to the invention, the first detector performs an extinction measurement, the second detector performs a fluorescence measurement, and the third detector performs a fluorescence measurement.

The measurements thus obtained allow the detection of some particularities, as brought to light for example by fluorochromes, or immunophenotyping in relation to the analyzed samples and the analysis of results conducted after the measurements have been taken.

According to a preferred characteristic, the two dichroic mirrors have identical optical properties generating the total reflection of wavelengths longer than the wavelength of the second source and shorter than the wavelengths of the first source.

With this characteristic, it is possible to modify at will the measurements associated with each detector without having to modify the physical structure of the device according to the invention.

According to one particular characteristic of the invention, at least one other dichroic mirror is added in the emitting gun and/or receiving gun.

The addition of a second dichroic mirror having adapted characteristics in at least one of the guns makes the addition of another measurement possible at 90° from the main optical axis. The principle according to the invention can therefore be completed by adding several dichroic mirrors in each of the receiving and/or emitting guns. The multiplicity of measurements can therefore be further increased and the classification of particles is even more precise with the possible including of more classes.

BRIEF DESCRIPTION OF THE DRAWINGS

Other characteristics and advantages of the present invention will become apparent from the description below, with reference to the appended drawings that show one example of embodiment thereof that is in no way limiting. In the figures.

DETAILED DESCRIPTION OF ONE EMBODIMENT

Figure 1:
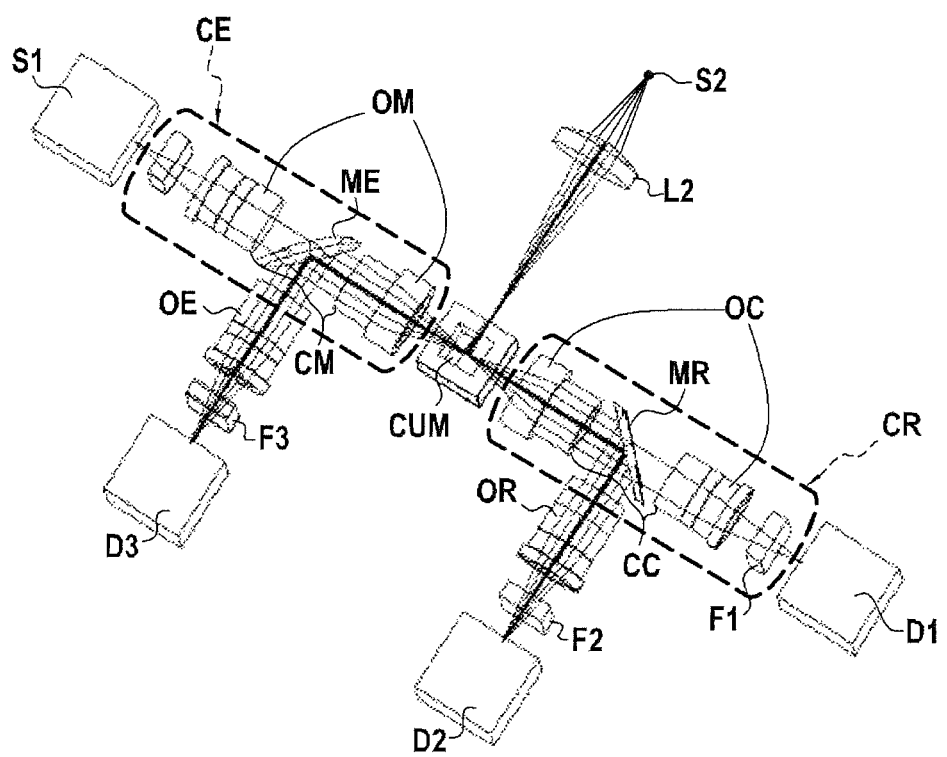
FIG. 1 shows a device according to the invention.

FIG. 1 schematically shows the structural and functional principles of a device according to the invention. The optical device comprises a focusing nozzle (not shown), at least two light sources S1 and S2, which may or may not be combined in the measuring chamber and capable of emitting in different spectral zones.

One of the two light sources S1 is of weak temporal coherency, with a coherence length Lc<100 μm at a central wavelength of 650 nm. It defines a first optical axis.

The second light source S2, positioned here at 90° from the optical axis of source S1, comprises one or more monochromatic sources such as those typically used for tri-parametric optical fluorescence detection, denoted FL1, FL2 and/or wide angle diffraction SSC (also known as side scatter), according to one of the chosen configurations described in the following. The light source S2 advantageously comprises a laser diode with a wavelength of 488 nm allowing fluorescence phenomena to be generated on cells labelled with Thiazole Orange.

A measuring chamber CUM is positioned at the intersection of the optical axes of the two light sources S1 and S2.

In one advantageous embodiment, a capillary directs the cell suspension into a focusing nozzle comprising a micro-orifice. A secondary fluid ensures centring of the cell suspension through the crossing of the measuring orifice. This orifice is used to implement volume measurement using an electrical method, typically a resistivity measurement. A constant current passes through this orifice. When a cell passes through the orifice, the resistivity of the channel is modified and produces a voltage variation at the terminals of the counting orifice. This voltage is proportional to the volume of the cell. This measuring method is known as the "Coulter Principle" and the electronic provisions for implementation thereof will not be described in this text.

The cells are then conveyed into an optical analysis window obtained by projecting a light intensity reticule that is as uniform as possible into the measuring chamber CUM. The light that is diffracted, reflected or absorbed by the particle perturbs the light propagation, which is detected by the device according to the invention.

According to one embodiment of the invention, two optical elements are arranged on the optical axis of the source S1: an emitting gun CE located between the source S1 and the measuring chamber CUM and a receiving gun CR located between the measuring chamber CUM and the detector D1.

The measuring chamber may have a circular cross-section. However, this generates substantial optical corrections that increase the cost of manufacturing the device according to the invention. In one advantageous embodiment, the measuring chamber is polygonal and has at least four sides of which at least two are parallel to each other. These two parallel sides are positioned so as to be perpendicular to the optical axis of the source S1. The optical axis of the second source S2 is perpendicular to another side of the measuring chamber CUM.

The preferred embodiment, according to which the axis of the second source S2 is perpendicular to the axis of the first source S1, advantageously uses a four-sided measuring chamber. This allows very simple, low-cost fabrication of the device according to the invention. Indeed, in this case, the optical corrections to be made for passage through the walls of the chamber are facilitated and the orientation of the optical axes is optimal.

The emitting gun CE comprises beam-shaping optics OM. These optics OM image a reticule onto the sample stream ejected by the nozzle and present in the measuring chamber CUM. The beam-shaping optics OM are such that the light beam is collimated over a portion of pathway denoted CM.

The receiving gun comprises collection optics OC to collect the image of the reticule towards the detector D1. Unless an extinction measurement is not required, the detector D1 performs an extinction measurement EXT. According to the invention, the collection optics OC are such that the light beam is collimated over a portion of pathway denoted CC.

The beam-shaping optics OM are such that, at the measuring chamber CUM, the numerical aperture of the convergent light beam is equal to ON1=n*sin u, wherein n is the optical index of air (hence n=1) and u is the half-aperture angle at the input to the beam-shaping optics OM.

Uniformity of illumination is conventionally obtained by a Köhler type assembly. The principle of Köhler illumination entails the imaging of the light source S1 in the collection optics OC. This makes it possible firstly to have a single image of the source S1 in the pupil of the collection optics OC and secondly to obtain uniform distribution of light in the image of the reticule.

The source S1 is advantageously a light-emitting diode with resonant cavity. These diodes have the advantage of exhibiting a clearly determined spectrum at wavelengths absorbed by the cells to be characterized. Therefore for extinction measurements, advantageous use is made of a light-emitting diode with resonant cavity having a spectral peak centred on the 650 nm wavelength and a bandwidth of 40 nm. However, it is known that such a diode emits in the red but has a harmonic in the green. It is therefore necessary to place a band-pass filter in the emitting gun CE to prevent this green component from disturbing the other measurements, such as fluorescence measurement, by generating background noise. Advantageously, the receiving gun comprises the same filter so as only to take the extinction signal into consideration.

The illumination system can be based on the use of an optical fibre conformed as indicated in the publication WO 2006/053960, in the name of the Applicant.

In general, the sizing of the optical bench is based on the size of a desired optical window and on the beam angle in the counting cell or measuring chamber. The image of the reticule is typically of rectangular shape and its dimensions are set by two constraints. The largest dimension is determined by the size of the sheathing fluid, this diameter being substantially that of the orifice used for volumetric measurement. It is therefore fixed at about 100 µm. The smallest dimension determines the spatial resolution of the measurement, which is the capacity to discriminate between two very close cells. Ideally, this dimension must be as small as possible. As the biological particle passes the illuminated window at a velocity v, the smallest dimension of the window defines the exposure time of the cell to the light flow and hence the duration of the electric pulse corresponding to physical extinction and diffraction phenomena along the axis. In practice, this dimension is in the order of 30 µm. It may be noted that the aspect ratio of the analysis window is then on the order of 3. It may also be noted that the numerical aperture of the beam of the receiving optics is equal to that of the illuminating beam. This gives ON2=ON1.

Advantageously, when the device operates in extinction mode EXT with detector D1, the illuminating beam has an angular opening between 1° and 60° and is chosen in relation with a range of volume, a refractive index range, and the intra-cytoplasmic composition of the particles being examined. It has the chosen central wavelength. It also has an illumination uniformity greater than 10% in a parallelepiped measuring volume a×b×c, where a×b is the rectangular cross-section of the beam whose aspect ratio a/b is lower than 4 and c is the field depth defined as the geometric interval around the measuring point for which the power does not vary by more than 10%. The value of this interval is typically in the region of 500 µm+/−250 µm.

Regarding the second light source S2, the positioning of its axis in a manner such that this optical axis crosses the axis of the first source S1 is particularly advantageous. Indeed, the optical axis of the least coherent light source S1, which emits at wavelengths centred around 650 nm and is typically used for extinction measurement, is aligned with the axis of the light detector D1, typically a photodiode. At the same time, the optical axis of the light source S2 for excitation of fluorescence and/or of diffraction is perpendicular to the optical axes of the detector D1 and of the other light source S1. It is noted here that the mere crossing of the optical axes with a distinct angle of 90° also allows the described advantages to be obtained.

This characteristic further allows good behaviour of the detector D1 for extinction, fluorescence, and diffraction if it is important to use the detector D1 for the measurement of one of these parameters. When the detector D1 operates in extinction mode, whereby the detector D1 measures an extinction parameter EXT, it is ensured that the detector D1 is well positioned facing the light source. Detection is therefore made against a light background. Advantageously, a filter F1 can be used for spectral filtering of the wavelengths emitted by the source S1.

When the detector D1 is used for fluorescence measurement, by placing the most coherent source S2, typically a laser, to induce fluorescence of the marker(s) or dyes present on or in the cell at the time when the cell passes over the optical pathway perpendicular to the detector D1, the architecture of device according to the invention allows the measurement to be taken against a black background. This is effectively important when fluorescence detection is performed in the extinction frequency band. In this case, detection of FL2 is performed in the extinction frequency band and the source S1 is switched off. Positioning at 90° has the advantage however of providing the device according to the invention with symmetry. In addition, this allows largely facilitated implementation. It is noted here that in this case, the detector D1 advantageously has switchable variable gain enabling it to measure light intensities that vary greatly, as indicated in patent FR 2 933 192 to the Applicant.

According to the invention, the device comprises two dichroic mirrors MR and ME appropriately chosen in relation to the parameters it is desired to measure. The first dichroic mirror MR is inserted in the receiving gun CR at the point where the light beam is collimated. The second dichroic mirror ME is inserted in the emitting gun CE and, in an original manner, makes use of the principle of the inverse return of light.

In the preferred embodiment of the invention, the two mirrors MR and ME are identical. They cause total reflection of wavelengths equal to or longer than the shortest of the wavelengths of the source or sources positioned at 90° and shorter than the wavelengths of the first source S1. The manufacturing costs of the device according to the invention are thereby limited. In the described example, these mirrors MR and ME therefore allow the passing of 98% of the red component emitted by the first source S1 and reflect the blue and green component of fluorescence FL1.

The mirrors MR and ME advantageously allow the separation of the wide angle diffraction components denoted SSC and/or fluorescence components caused by the interaction between the light emitted by the source S2 and the cell being observed. Thus, this optical assembly in particular allows the easy separation of cell populations, for example the 8 populations of nucleated cells in a whole blood sample, since it provides hitherto unknown diversity of parameter measurements within a single device.

According to the invention, the optical assembly is simpler than prior art devices. Use of the principle of the inverse return of light allows a wide angle diffraction measurement or fluorescence measurement to be added, without modifying the general structure of the device but rather solely by adding dichroic mirrors.

To perform these measurements, the source S2 is activated. The light emitted by the source S2 is focused by means of a convergent lens L2 in the plane perpendicular to the plane of extinction measurement. The image obtained at the point of measurement is an ellipse that measures about 100 μm×30 μm, for the same reasons as given previously. Since the source S2 is a laser diode and therefore has an elliptical beam, previously chosen to have an output ratio of 1/3, it is not necessary to insert an optical system, which is generally quite expensive, to shape the beam as is well known to the person skilled in the art.

The light issued by the interaction between the light emitted by the source S2 and the cell follows an inverse pathway in the emitting gun. The diffraction component is separated from the extinction component by the dichroic mirror ME placed in the emitting gun. The light issued by fluorescence is separated from the extinction component by the dichroic mirror MR placed in the receiving gun.

The wide angle diffracted light, SSC, is collected by the beam-shaping optics OM of the emitting gun CE in accordance with the principle of the inverse return of light. The dichroic mirror ME, inserted in the beam-shaping optics OM, allows this component to be reflected 90° from the extinction axis towards a detector D3.

Since fluorescence is isotropic, i.e. it emits light rays uniformly in all directions in space, a band-pass filter, denoted F3, centred on the wavelength of the source S2 allows the elimination of the fluorescence component from the wide angle diffraction measurement SSC performed by the detector D3. The filter F3 is advantageously a band-pass filter centred on 488 nm with a blocking of $10^{-6}$ on the fluorescence component. The association of the beam-shaping optics OM, the filter F3, and the detector D3 allows the wide angle diffraction measurement SSC to be performed. Advantageously, additional optics denoted OE, are placed after the dichroic mirror ME, between this mirror and the detector D3. These optics OE allow the diffracted beam coming from the dichroic mirror ME to be focused onto the detector D3.

The fluorescence FL1 is collected by the collection optics OC of the receiving gun CR. The dichroic mirror MR, inserted in the collection optics OC, allows this component to be reflected 90° from the optical axis of the source S1 towards a detector D2. To separate the diffractive component, a band-pass filter F2, centred on the expected fluorescence peak of FL1, is inserted in the optical pathway between the dichroic mirror MR and the detector D2. The filter F2 is advantageously a band-pass filter centred on 530 nm associated with double NOTCH filter which eliminates, via a blocking of $10^{-8}$, the diffraction component, which is on average 1,000 times greater than the fluorescence component with Thiazole Orange marking and the red component issued by the first source S1. The association of the collection optics OC, the filter F2, and the detector D2 allows the fluorescence measurement denoted FL1 to be performed.

Advantageously, an additional optic denoted OR, is placed after the dichroic mirror MR, between this mirror and the detector D2. This optic OR allow the fluorescence beam issued by the dichroic mirror MR to be focused onto the detector D2.

The configuration of the assembly according to the invention is such that fluorescence FL1 and the wide angle diffraction SSC are collected by a part of the optics also intended for extinction measurement EXT. With this approach, an optimal integration level, characteristic of the invention, is obtained. A reduction in manufacturing costs and facilitated implementation are therefore major advantages of this invention.

With such a device, each cell is measured in four parameters, namely resistivity, extinction, fluorescence and wide angle diffraction measurements.

The device according to the invention therefore comprises optics OC associated with a filter F1 providing wavelength filtering of the reticule image, an optic OE with a band-pass filter F3 centred on the wavelength of the source S2 collecting the wide angle diffraction SSC produced by the interaction between the light emitted by the source S2 and the cell being observed, an optic OR, a band-pass filter F2 centred on the fluorescence peak and collecting the fluorescence produced by the interaction between the light emitted by the source S2 and the cell and two dichroic mirrors MR and ME allowing separation firstly of the diffraction and extinction components and secondly of the fluorescence and extinction components, and finally three detectors D1, D2 and D3 which are three photodiodes or preferably two photodiodes and one variable gain avalanche photodiode respectively.

Conventionally, the fluorescence and diffraction lights are separated on the basis of their spectral properties. For this purpose, interference optical filters F1, F2, F3 of multi-dielectric type, i.e. filters obtained by alternately depositing two or more transparent materials having different indexes of refraction, are generally used. Advantageously, they are ion bombarded filters that impart very good off-band blocking and very good transmission. These filters F1, F2, F3 are installed on the light paths between the measuring chamber CUM and the detectors D1, D2, D3 in accordance with the desired measurements. Various filters can be used in relation to the expected fluorescence wavelengths and the implemented illumination wavelengths.

The device according to the invention can therefore be modulated by choosing to extract the most relevant parameters for the intended application: counting and differentiation of leukocytes, immunophenotyping or detection of certain particular characteristics of the cell populations contained in the sample, and so forth. Indeed, extinction causes the intervention, in a large measure, of cell refraction/diffraction phenomena. If Thiazole orange is used, fluorescence characterizes the RNA content of each cell. Finally, wide angle diffraction SSC reflects cell lobularity. This set of measurements allows a sufficient amount of reliable data to be obtained giving results that are sensitive and specific to the examined cell populations.

The modulations may include for example:
Resistivity RES, Extinction EXT, wide angle diffraction SSC, and Fluorescence FL1 for the counting and the differentiation of 8 populations of nucleated cells;
Resistivity RES, Extinction EXT, two Fluorescences, FL1 and FL2, for the detection of certain particularities for example as evidenced by fluorochromes;
Resistivity RES, Extinction EXT or one Fluorescence FL2, wide angle diffraction SSC, and one Fluorescence FL1 for application to immunophenotyping.

When the wide angle measurement SSC is replaced by a second fluorescence FL2, the band-pass filter centred on the wavelength of the source S2 is replaced by the same type of filter centred on the emission peak of the fluorescence FL2. It is to be noted that the beams emitted by S1 and S2 must then be combined at the measurement point. It is only in this case that it would be judicious to use time-shifting of the measurements of fluorescence FL1 and FL2 emitted by two monochromatic sources S2 and S3 used for fluorescence measurements, the latter source S3 being placed at the same position as the source S2. The measurement of the second fluorescence can be performed on the detector D3 positioned on the side of the emitting gun CE or it can be performed on D1 also used for the extinction measurement. In this case, the detector D1 has a switchable gain so as to be able to measure intensities of very different orders of magnitude.

The second fluorescence is advantageously fluorescence on a leukocyte marker of the CD45 type. This marker has the feature of causing fluorescence around 665 nm, which corresponds to the bandwidth of the diode forming the first source S1. With this fluorescence it is possible to avoid having to change filters on the optical path towards the detector D1. Indeed, to access the fluorescence measurement on the detector D1, the sole obligation is to switch off the first source S1 when labelling with CD45. The measurement of this second fluorescence is then conducted with the detector D1 switched over to avalanche mode.

In another configuration, the band-pass filter F3 can be replaced by the same type of filter centred on the fluorescence peak FL2. In this case, the addition of a second monochromatic source, also situated at 90° from the axis of the source S1, allows the second fluorescence to be measured. It is to be noted that in this precise case, it is preferable for the fluorescence measurements to be time shifted to prevent the compensation phenomenon known to the person skilled in the art.

A fifth parameter measuring small angle diffraction (also known as Forward Scatter FSC) can be added in certain applications by placing a detector in the axis of the laser. It may be noted that this detector may be used to trigger optical measurements. A resistivity measurement is then advantageously associated therewith to obtain volumetric data in addition to an absolute count. These parameters also allow platelets (the smallest elements in blood) to be characterized using the same device.

The device described in the foregoing is used for the identification and characterization of erythroblasts and of seven leukocyte populations, namely lymphocytes, monocytes, neutrophils, eosinophils, basophils, immature granulocytes, and immature cells.

This device for analysing biological fluid is connected to receiving means to receive measured data corresponding to n=4 physical parameters: resistivity height RES, height SSC, extinction height EXT, and height FL1. Advantageously, the fluorescence parameter FL1=TO for Thiazole Orange corresponds to fluorescence after labelling with Thiazole Orange. In its basic version, the reagent "Fluowhite" (subject of patent FR 2 821 428 and manufactured by Horiba Medical) allows a total lysis of the red blood cells whilst preserving and labelling with Thiazole Orange all the nucleated cells contained in whole blood. These n parameters define an event.

Each event is then classified into one of the eight cell populations presented above. The viewing means are matrices, i.e. orthogonal spaces each using two measurement parameters.

The four usual matrices allowing this viewing are in general: RES×EXT, SSC×FL1, EXT×FL1, and EXT×SSC.

In the case of blood not exhibiting any pathology, the measurements RES and EXT are sufficient for a full identification of the lymphocyte L, monocyte M, neutrophil N, and eosinophil E populations.

Figure 2:
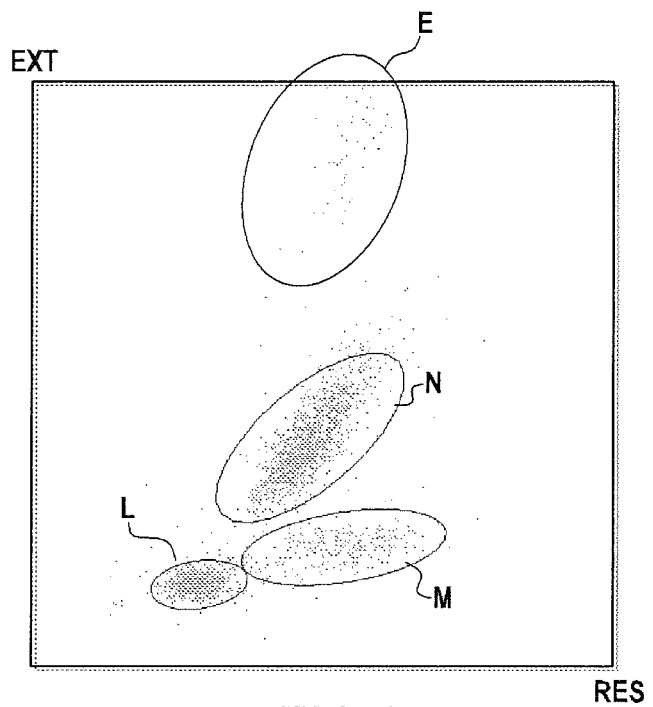
FIG. 2 shows a cell classification, obtained by means of a device according to the invention, for a blood sample without a pathology and obtained with resistivity RES and extinction EXT parameters.

FIG. 2 shows a cell classification for blood not exhibiting any pathology.

However, these measurements do not allow the identification of basophils, erythroblasts, immature granulocytes, and immature cells. Since these populations often relate to a particular pathology, it is important to be able to identify these and to obtain the most precise count possible.

Figure 3:
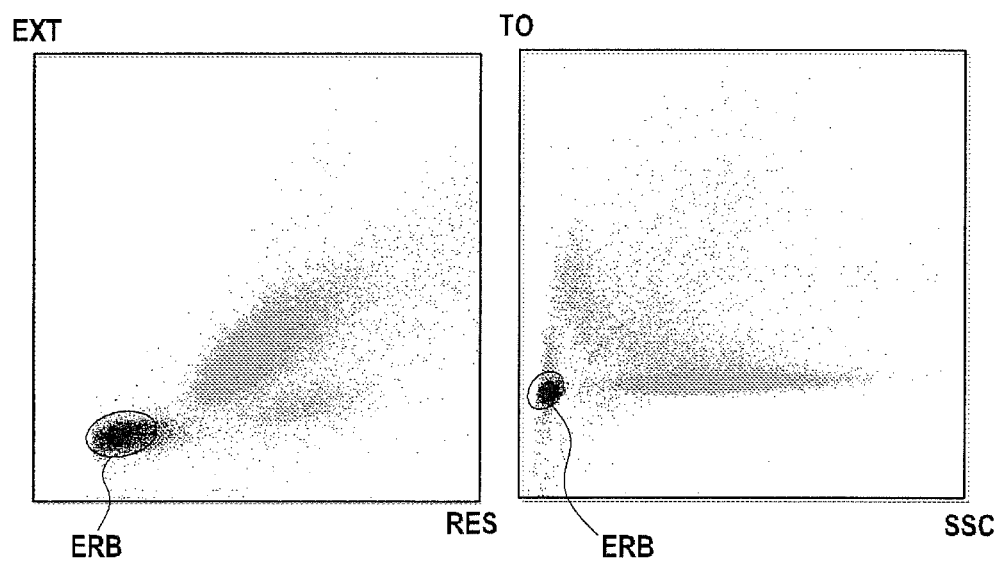
FIG. 3 shows a cell classification, obtained by means of a device according to the invention, for a blood sample containing erythroblasts, obtained with resistivity RES, extinction EXT, and fluorescence FL1=TO parameters.

The device according to the invention allows a precise identification of erythroblasts by means of the fluorescence measurement FL1 allowed by the invention. Erythroblasts may display the same resistivity height, the same extinction height, and the same SSC height as lymphocytes. However, after incubating the sample with Thiazole Orange specific to nucleic acids, the erythroblasts have a weaker fluorescence response than lymphocytes. Thus, the measurement of fluorescence FL1 is important for correct identification of erythroblasts. FIG. 3 shows this advantage for blood containing erythroblasts represented by encircled black dots ERB. It is noted here and for the remainder of the description that only some of the dots seen in the encircled regions represent identified populations, these being the black dots. The encircling of regions is used for graphical reasons only.

Figure 4:
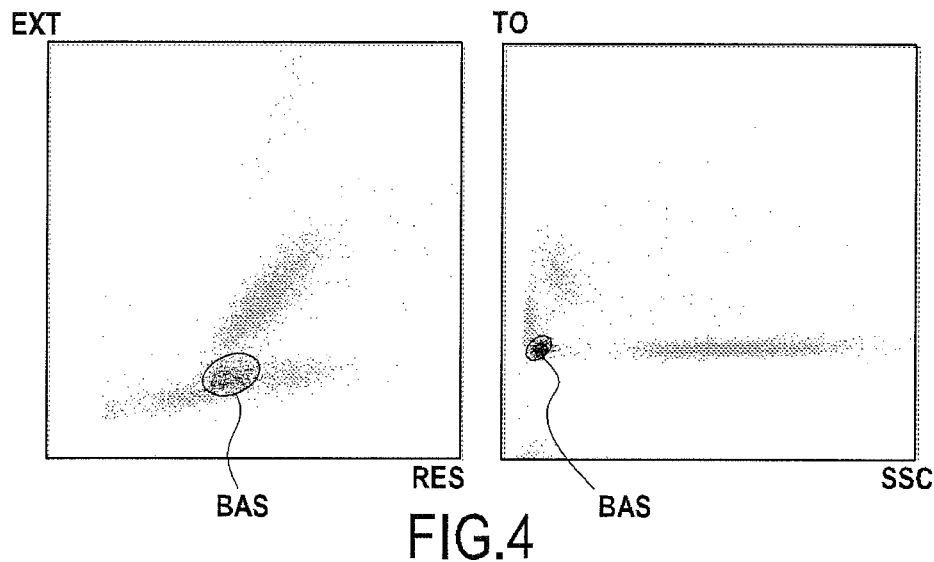
FIG. 4 shows a cell classification, obtained by means of a device according to the invention, for a blood sample containing basophils, obtained with resistivity RES, extinction EXT, fluorescence FL1=TO, and side scatter SSC parameters.

After having incubated the sample with Thiazole Orange, the device allows a precise identification of basophils by means of the fluorescence measurement FL1 and the wide angle diffraction measurement SSC. The basophils have a highly scattered position in the RES×EXT matrix and can easily be confused with lymphocytes, monocytes, and neutrophils. Therefore, in the event that basophils are present, the identification of these populations with the measurements RES and EXT alone is impossible. On the other hand, the basophils are easily identifiable in the SSC×FL1 matrix as shown in FIG. 4. The basophils are represented by encircled black dots BAS.

The device allows precise identification of immature granulocytes by means of the matrix EXT×FL1. The fluorescence measurement FL1, again with Thiazole Orange, allows the maturity of the granulocytes, neutrophils, or immature granulocytes to be determined. The immature granulocytes may have the same resistivity heights SSC and FL1 as monocytes. Therefore, for perfect identification thereof, the extinction EXT and the fluorescence FL1 measurements are needed. The matrix SSC×FL1 is less discriminatory; however, it is used in the event of hypo-granulation of neutrophils and immature granulocytes.

Figure 5:
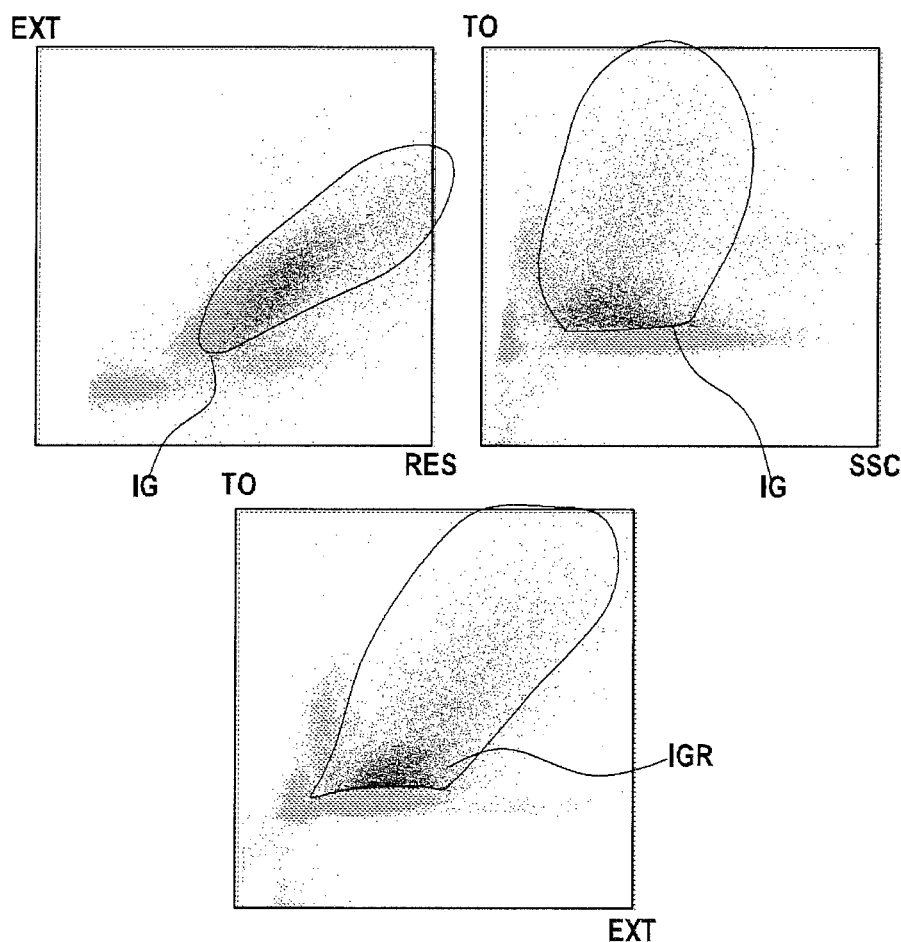
FIG. 5 shows a cell classification, obtained by means of a device according to the invention, for a blood sample containing immature granulocytes, obtained with resistivity RES, extinction EXT, fluorescence FL1=TO, and side scatter SSC parameters.

FIG. 5 shows this advantage for a case in which a blood sample contains immature granulocytes represented by encircled black dots IG.

Figure 6:
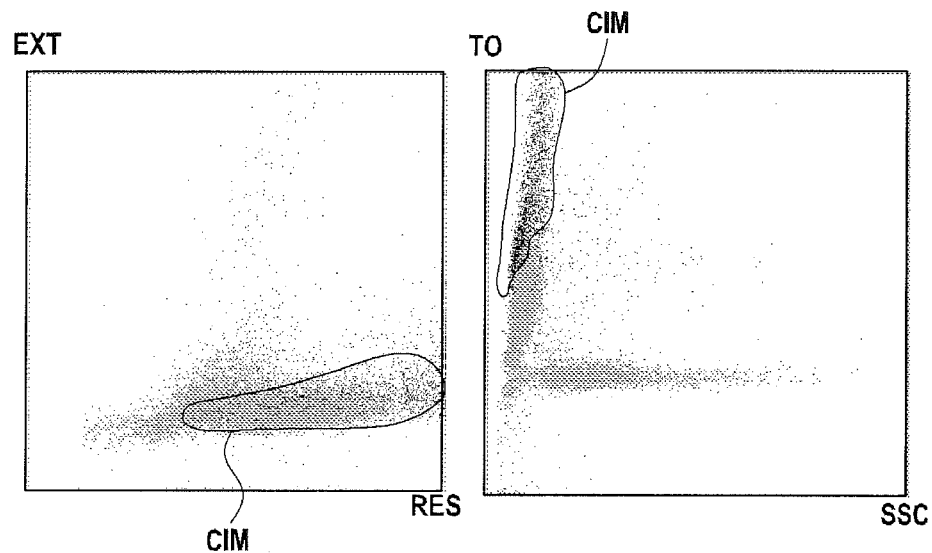
FIG. 6 shows a cell classification, obtained by means of a device according to the invention, for a blood sample containing immature cells, obtained with resistivity RES, extinction EXT, and fluorescence FL1=TO parameters.

The device according to the invention allows a precise identification of immature cells by means of the fluorescence measurement again with Thiazole Orange. Since immature cells contain more RNA than mature cells, they give a higher fluorescence response. FIG. 6 shows this advantage. It can be seen that the immature cells represented by black dots being counted among the encircled particles CIM are better differentiated in the diagram (SSC, TO) than in the diagram (ABS, RES). The two Figures taken together however allow good differentiation.

Figure 7:
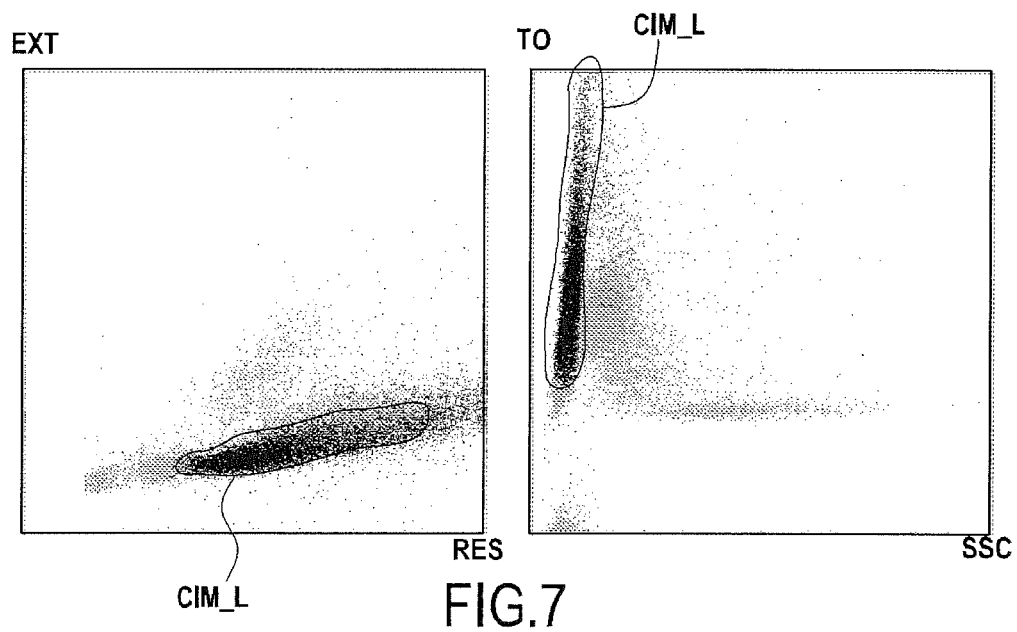
FIG. 7 shows a cell classification, obtained by means of a device according to the invention, in a case of lymphoid leukaemia, obtained with resistivity RES, extinction EXT, fluorescence FL1=TO, and side scatter SSC parameters.

The device further allows a precise identification of immature cells in cases of lymphoid pathology by means of the measurement SSC. Lymphoblasts have the same resistive, extinction, and FL1 heights as monocytes. Therefore, for perfect identification thereof an additional measurement SSC is required. FIG. 7 shows this advantage in a case of lymphoid leukaemia. The lymphoblasts here are represented by encircled black dots CIM-L.

The device advantageously allows the identification of the seven leukocyte populations and of erythroblasts in normal blood samples and in pathological blood samples. In addition, it also shows its superiority for pathologies frequently encountered on mature cells.

Figure 8A:
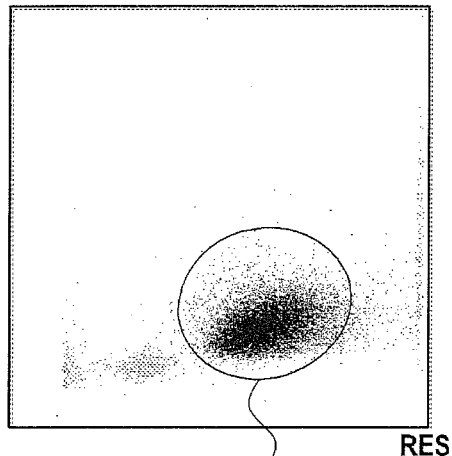
FIGS. 8a and 8b show common matrices obtained by means of a device according to the invention and a prior art device, in a case of myelodysplastic blood using resistivity RES, extinction EXT, and fluorescence FL1=TO parameters.
Figure 8C:
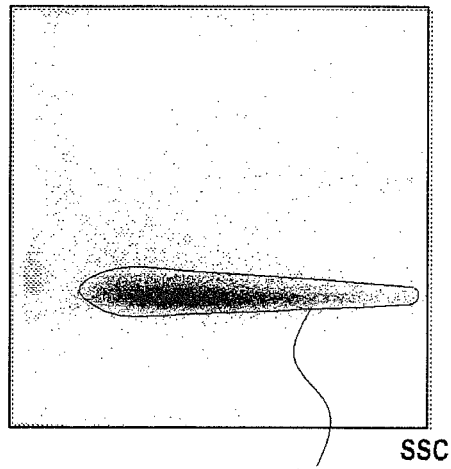
FIG. 8c shows a matrix obtained solely by means of a device according to the invention using the new parameter of side scatter measurement SSC.
Figure 8B:
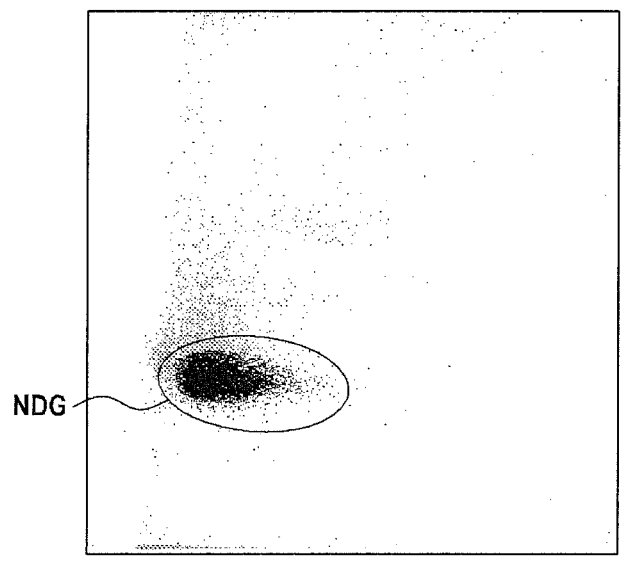

FIGS. 8a and 8b show the common matrices obtained using the device according to the invention and a prior art device for parameters of resistivity RES, extinction EXT, fluorescence FL1=TO, in a myelodysplastic blood sample. In these matrices, it is impossible to identify the degranulated neutrophils NDG, which are merged with the monocytes and lymphocytes. FIG. 8c, on the contrary, shows a matrix obtained solely with a device according to the invention using the new measurement parameter of wide angle diffraction SSC, which allows an identification of the degranulated neutrophils NDG.

Figure 9:
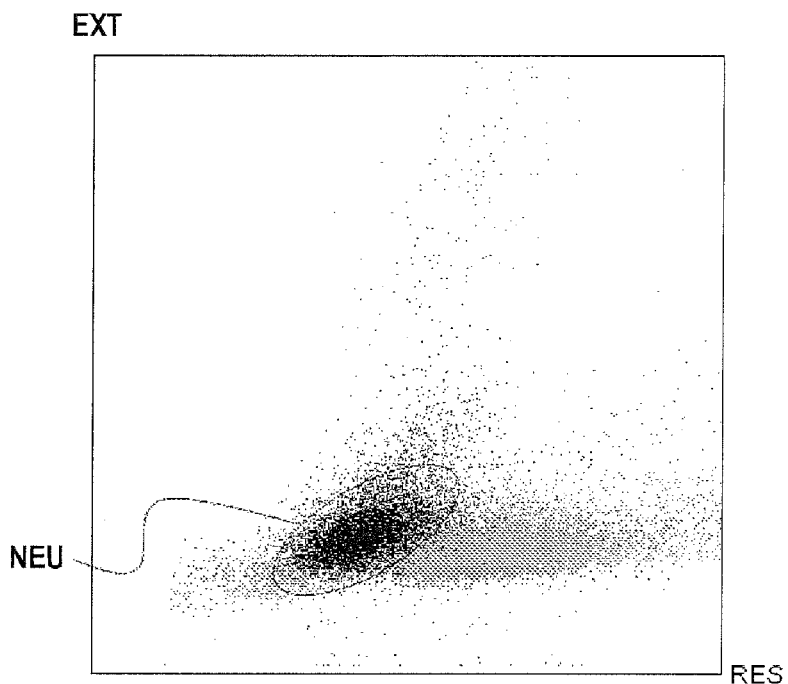
FIG. 9 shows blood with neutrophils having a very low refractive index, this figure being obtained by extinction measurement EXT.

The device according to the invention further allows characterization of the granulation of neutrophils by means of the extinction measurement EXT. The presence of granulations increases the extinction height EXT, which is why neutrophils and eosinophils have higher extinction EXT than lymphocytes and monocytes, which do not have granulation. It is therefore possible to define a granulation index. This is calculated as the mean of the refractive indexes of the neutrophils. FIG. 9 shows a blood sample wherein the neutrophils, represented by encircled black dots NEU, have a very low refractive index.

Figure 10:
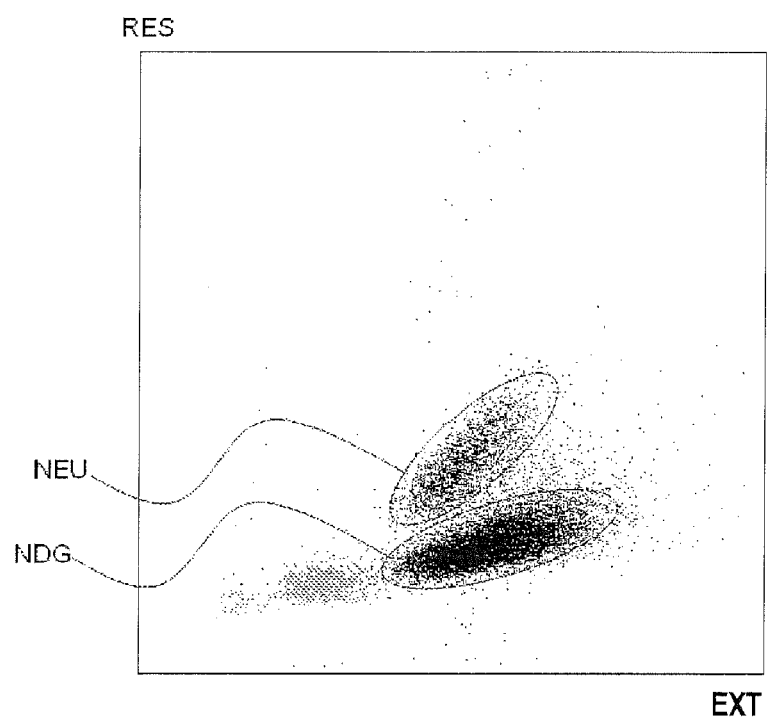
FIG. 10 shows blood whose neutrophils have two different indexes of refraction distinguished on the basis of extinction measurement EXT.

The device according to the invention also allows the "alerting" of a blood sample that contains a population of normal neutrophils and a population of degranulated neutrophils. This translates as the presence of neutrophils having two different refractive indices. This can be detected by using the extinction measurement EXT. FIG. 10 shows a blood sample whose neutrophils, represented by encircled black dots NEU and NDG, have two different refractive indices.

Figure 11:
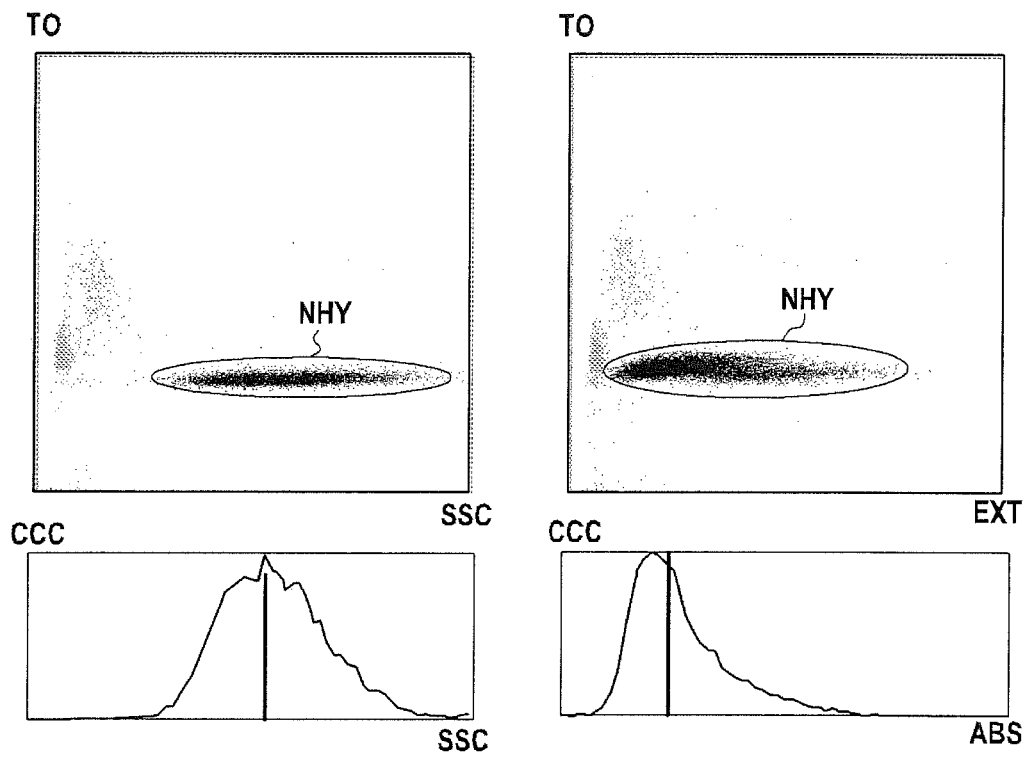
FIG. 11 shows the case of blood having hypo-segmented neutrophils, on the basis of side scatter measurement SSC.

The device according to the invention allows neutrophil lobularity to be characterized by means of a measurement SSC, which is highly sensitive to the internal structure of a cell and therefore reflects the shape of the nucleus. Thus, the higher the number of nucleus lobes, the higher SSC height and vise versa. It is therefore possible to define a lobularity index as the mean of the SSC heights of the neutrophils. FIG. 11 shows the case of a blood sample with hypo-segmented neutrophils which are represented by encircled black dots NHY.

Figure 12:
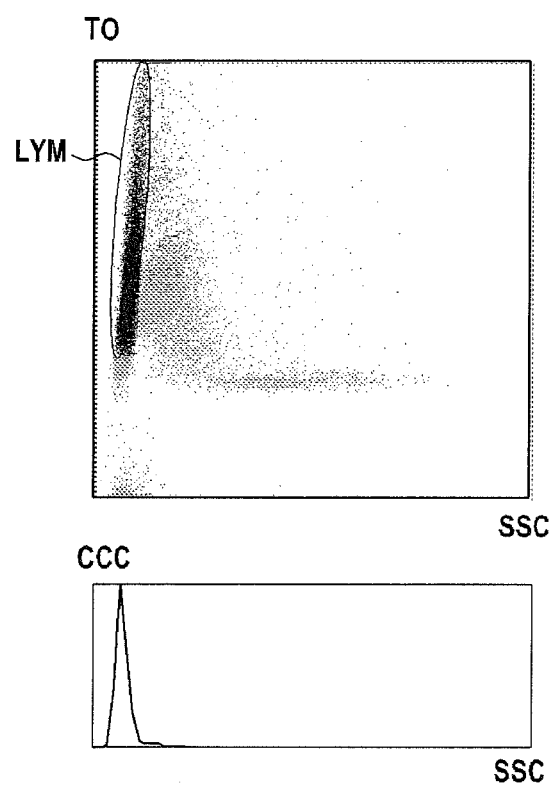
FIG. 12 shows lymphoblastic characterization of immature cells in blood, on the basis of side scatter measurement SSC.

The device according to the invention allows the type of immature cells to be characterized by means of a measurement SSC. The smaller the SSC mean of the immature cells, the more likely they are lymphoblasts. The SSC mean for lymphoblasts is in the region of 245, for monocytes it is about 644, and for HRCs (High RNA Content) about 322. FIG. 12 shows lymphoblastic characterization of the immature cells in a blood sample. The lymphoblasts are represented by encircled black dots LYM.

It is to be noted that this device may also allow red blood cells of different shapes and sizes to be brought to light. It is therefore possible for example to bring to light red blood cells having inclusions, sickle cells, etc. To do so, the device according to the invention comprises two fluorescence measurements taking place at different illumination wavelengths. Special filters are then used.

The advantage of immunophenotyping by flow cytometry (FCM) in clinical biology concerns numerous fields and in particular:

The description of normal populations in blood, bone marrow, and different organs;
The analysis of antigens of leukocyte differentiation;
The study of cell birth, life, and death;
The description of mechanisms of cell signalling and different cell functions;
The investigation of immunopathology topics: diagnosis and monitoring of immune deficiency, diagnosis and monitoring of auto-immune diseases, immunology of grafts and transplants, lymphoproliferative diseases, hypersensitivities;
The contribution to the diagnosis of numerous haematological diseases; and
The evaluation, in the field of cancerology, of host reactions against tumours and immunotherapy follow-up.

The possible identification by flow cytometry of cell antigens in relation with the study of nucleic acids, of the cell cycle, and of ploidy has taken a large step forward in the study of physiopathological mechanisms of various diseases.

In the event of application of the device according to the invention to immunophenotyping, the photodiode allowing extinction to be detected is replaced by an avalanche photodiode connected to a polarization circuit capable of inhibiting internal avalanche gain. With this implementation it is possible to reduce the behaviour of the avalanche photodiode to behaviour of a conventional unitary gain photodiode such as conventionally used for extinction measurement EXT. If there is no gain inhibition, the avalanche photodiode would saturate if used for extinction measurement with high light intensity. This method is described in patent FR 2 933 192 to the Applicant.

Finally, it is pointed out that various embodiments can use the principles according to the invention. In particular, other dichroic mirrors can be installed in series in the receiving gun and in the emitting gun of the device according to the invention to deflect the light beam originating from the measurement chamber towards detectors taking other measurements. The dichroic mirrors will then all be different so as to direct the components of the light flow towards each of the detectors. This embodiment, which further multiplies the number of accessible measurements, has the disadvantage however of being costly to implement on account of the diversity and precision of the mirrors which need to be used. It is also to be noted that the use of a measuring chamber having a higher number of sides than in the described example, e.g. 6 or 8 sides would allow the multiplication of measurements following the principles according to the invention.

The invention claimed is:

1. An electro-optical flow measuring device for the characterization of microparticles, comprising:
    a first optical axis comprising, from one extremity to another, a first light source, an emitting gun, a measuring chamber, a receiving gun, and a first detector, the first light source and the first detector being arranged facing each other at opposite ends of the first optical axis,
    a second optical axis, perpendicular to the first optical axis, comprising from one extremity to another, a second light source and the measuring chamber, the measuring chamber being arranged along the first optical axis at the intersection of the first optical axis and the secondary optical axis,
    a third optical axis, perpendicular to the first optical axis, comprising from one extremity to another a second detector and a first dichroic mirror arranged in the emitting gun, and
    a fourth optical axis, perpendicular to the first optical axes, comprising from one extremity to another a third detector and a second dichroic mirror arranged in the receiving gun, and
    wherein the emitting gun comprises:
        beam-shaping optics for shaping the beam emitted by the first light source such that the light beam is collimated over a portion of its pathway, and
        the first dichroic mirror placed at the portion of the pathway where the light beam is collimated, so as to partly reflect the beam issued from the interaction between the second light source and the particles in the flow towards the second detector along the third optical axis,
    wherein the receiving gun comprises:
        collection optics collecting the beam issued from the interaction between the first light source and the particles in the flow towards the first detector such that the transmitted light beam is collimated over a portion of its pathway, and the second dichroic mirror placed in the receiving gun at the portion of pathway where the light beam is collimated, so that it partly reflects the light beam issued from the interaction between the second light source and the particles in the flow towards the third detector along the fourth optical axis, and a device for measuring resistivity, wherein:

the first, second, third, and fourth optical axes are within a first plane, a fluid comprising the microparticles to be characterized circulates in the measuring chamber perpendicular to the first plane formed by the axes, the first, second, and third detectors each allow an optical parameter to be measured, the optical parameters chosen from among fluorescence, extinction, wide angle diffraction, and small angle diffraction, the first and second light sources are of disjoint spectra, the first light source being the least coherent and having the longest wavelength, and the second light source being the most coherent and having the shortest wavelength.

2. The device according to claim 1, wherein a diffraction/scatter detector is placed facing the second light source on the other side of the measuring chamber.

3. The device according to claim 1, wherein the first detector has switchable gain configured to perform two types of measurement, one being extinction measurement and another chosen from among diffractions and fluorescences.

4. The device according to claim 1, wherein the first detector performs an extinction measurement, the second detector performs a wide angle diffraction measurement and the third detector performs a fluorescence measurement.

5. The device according to claim 1, wherein the first detector performs an extinction measurement, the second detector performs a fluorescence measurement, and the third detector performs a fluorescence measurement.

6. The device according to claim 1, wherein the two dichroic mirrors have identical optical properties generating the total reflection of wavelengths longer than the wavelength of the second source and shorter than the wavelengths of the first source.

7. The device according to claim 1, wherein at least one other dichroic mirror is added in the emitting gun and/or receiving gun.

8. The device according to claim 1, wherein the measuring chamber is polygonal, having at least four sides of which at least two are parallel to each other.

9. The device according to claim 8, wherein the at least two parallel sides are positioned so as to be perpendicular to the first optical axis.

10. The device according to claim 1, further comprising a band-pass filter arranged on the third optical axis between the first dichroic mirror and the second detector.

11. The device according to claim 1, further comprising additional optics arranged on the third optical axis between the first dichroic mirror and the second detector.

12. The device according to claim 1, further comprising a band-pass filter arranged on the fourth optical axis between the second dichroic mirror and the third detector.

13. The device according to claim 1, further comprising additional optics arranged on the fourth optical axis between the second dichroic mirror and the third detector.

14. The device according to claim 1, wherein the receiving gun further comprises a filter for spectral filtering of the wavelengths emitted by the first light source.

\* \* \* \* \*